(12) United States Patent
Tsuji (10) Patent No.: US 7,738,091 B2
(45) Date of Patent: Jun. 15, 2010

(54) VISUAL INSPECTION APPARATUS

(75) Inventor: Haruyuki Tsuji, Ina (JP)

(73) Assignee: Olympus Corporation, Tokyo (JP)

( * ) Notice: Subject to any disclaimer, the term of this patent is extended or adjusted under 35 U.S.C. 154(b) by 3 days.

(21) Appl. No.: 12/152,578

(22) Filed: May 15, 2008

(65) Prior Publication Data

US 2008/0285022 A1 Nov. 20, 2008

(30) Foreign Application Priority Data

May 16, 2007 (JP) ............................ P2007-130196

(51) Int. Cl.
*G01N 21/00* (2006.01)
(52) U.S. Cl. .................. 356/237.4; 356/237.1
(58) Field of Classification Search ... 356/237.1–237.6, 356/243.4, 243.7, 600, 601, 239.3, 238.1, 356/239.7
See application file for complete search history.

(56) References Cited

U.S. PATENT DOCUMENTS 6,606,154 B1 * 8/2003 Oda ........................... 356/244

2006/0215152 A1 * 9/2006 Hashimoto ............... 356/237.2

FOREIGN PATENT DOCUMENTS

| JP | 10-092887 A | 4/1998 |
| JP | 2006-170622 A | 6/2006 |

* cited by examiner

*Primary Examiner*—Gregory J Toatley, Jr.
*Assistant Examiner*—Tri T Ton
(74) *Attorney, Agent, or Firm*—Frishauf, Holtz, Goodman & Chick, P.C.

(57) ABSTRACT

A visual inspection apparatus includes: a first substrate holding portion that holds a substrate so that a top surface is observable; a second substrate holding portion that holds the substrate so that a bottom surface is observable; a first substrate holding portion moving mechanism that moves the first substrate holding portion; a second substrate holding portion moving mechanism that moves the second substrate holding portion; and a control device that controls the first substrate holding portion moving mechanism and the second substrate holding portion moving mechanism so that the position of the substrate when observing the top surface of the substrate in the first substrate holding portion substantially matches the position of the substrate when observing the bottom surface of the substrate in the second substrate holding portion.

10 Claims, 10 Drawing Sheets

VISUAL INSPECTION APPARATUS

BACKGROUND OF THE INVENTION

1. Field of the Invention

The present invention relates to an inspection apparatus that inspects top and bottom surfaces of a substrate, such as a wafer.

Priority is claimed on Japanese Patent Application No. 2007-130196, filed May 16, 2007, the content of which is incorporated herein by reference.

2. Description of Related Art

In a semiconductor manufacturing process in the related art, it is known that visual inspection is performed by visual observation or imaging using an imaging device in order to check foreign matter adhering to a surface of a substrate, such as a wafer, film unevenness at the time of application of a resist, failure in exposure performed by an exposure apparatus, and the like. Examples of visual inspection include macro inspection for performing macroscopic inspection and micro inspection for performing enlarged observation using a microscope.

Here, an example of a visual inspection apparatus that performs macro inspection is disclosed in Japanese Unexamined Patent Application Publication No. 2006-170622. The visual inspection apparatus has a substrate holding unit, and a mechanism for performing rotation and rocking of a substrate is provided in the substrate holding unit. An illuminating device that illuminates a substrate is provided above the substrate holding unit. An inspector observes the substrate surface illuminated by the illuminating device by visual observation or using an imaging device. The visual inspection apparatus is used to record a result of visual inspection or share information on defects and the like in the case when a plurality of inspectors are present and is disposed such that an optical axis of an imaging device is substantially equal to the observation position of an inspector. Accordingly, observation and recording corresponding to an observer's observation may be performed.

Moreover, in recent years, it has also been desired to inspect a bottom surface of a substrate. An example of a visual inspection apparatus capable of observing a bottom surface of a substrate is disclosed in Japanese Unexamined Patent Application Publication No. 10-92887. The visual inspection apparatus includes a holding arm for holding the peripheral edge of the substrate, and a rotary shaft is provided at a base end of the holding arm. When the holding arm is disposed in the substantially horizontal direction, an observer can inspect a top surface of a substrate visually. When observing a bottom surface of the substrate, the holding arm is made to move upward by rotation of the rotary axis until the bottom surface of the substrate faces the observer.

SUMMARY OF THE INVENTION

According to an aspect of the present invention, a visual inspection apparatus includes: a first substrate holding portion that holds a substrate so that a top surface is observable; a second substrate holding portion that holds the substrate so that a bottom surface is observable; a first substrate holding portion moving mechanism that moves the first substrate holding portion; a second substrate holding portion moving mechanism that moves the second substrate holding portion; and a control device that controls the first substrate holding portion moving mechanism and the second substrate holding portion moving mechanism so that the position of the substrate when observing the top surface of the substrate in the first substrate holding portion substantially matches the position of the substrate when observing the bottom surface of the substrate in the second substrate holding portion.

In the visual inspection apparatus, when performing top surface inspection, the substrate is held on the first substrate holding portion and the first substrate holding portion moving mechanism is driven to move the substrate up to the inspection position. When performing bottom surface inspection, the substrate is held on the second substrate holding portion and the second substrate holding portion moving mechanism is driven to move the substrate up to a position substantially equal to the inspection position at the time of top surface inspection. In the case when the bottom surface inspection is first executed, the first substrate holding portion moving mechanism moves the substrate up to a position substantially equal to the inspection position at the time of bottom surface inspection.

DETAILED DESCRIPTION OF THE INVENTION

Embodiments of the invention will be described in detail with reference to the accompanying drawings. Moreover, in the following embodiments, the same constituent components are denoted by the same reference numerals. In addition, repetitious explanations will be omitted.

First Embodiment

Figure 1:
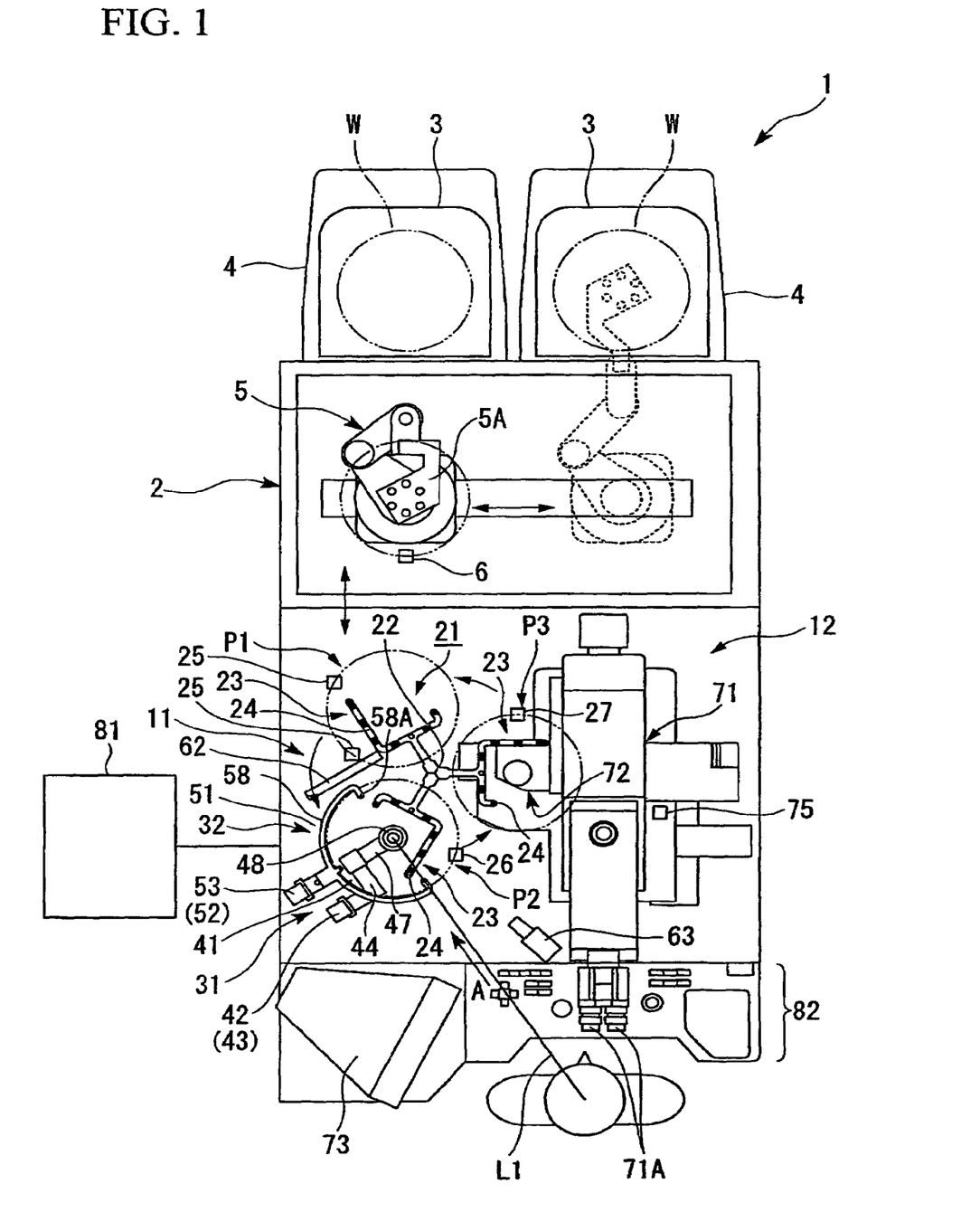
FIG. 1 is a plan view illustrating the configuration of a visual inspection apparatus.

As shown in FIG. 1, a visual inspection apparatus 1 is provided with two load ports 4 serving to attach a wafer carrier 3 to a back surface portion of a main apparatus body 2. A robotic transfer device 5 that takes out a substrate W, which is a wafer, from the wafer carrier 3 is disposed in the main apparatus body 2. The robotic transfer device 5 has a hand 5A provided to suction and hold one substrate W at the tip of an arm from below. A wafer detecting sensor 6 that detects the existence of the substrate W is provided at the position where the robotic transfer device 5 waits in an initial state. For example, an optically transmissive sensor or an optically reflective sensor is used as the wafer detecting sensor 6.

At a front side from the robotic transfer device 5, a macro inspection unit 11 for macroscopically observing the appearance of the substrate W by visual observation and a micro inspection unit 12 for performing an enlargement observation of the substrate W using a microscope are disposed on the left and right.

The macro inspection unit 11 has a rotary transfer device 21 that receives the substrate W from the robotic transfer device 5 and moves the substrate W to a predetermined position. The rotary transfer device 21 has a rotary shaft 22 extending in the vertically upward direction, and arm portions 23 are provided at the tip of the rotary shaft 22. The arm portions 23 are radially disposed at intervals of 120° in the circumferential direction and are unitarily formed so that the arm portions 23 move up and down simultaneously. A support portion 24 that suctions and holds the outer edge of the substrate W from below is provided at the tip of each arm portion 23. Rotation of the rotary transfer device 21 is controlled such that the arm portions 23 are disposed to circulate through a first position P1, a second position P2, and a third position P3. The first position P1 is a position where the substrate W is delivered from/to the robotic transfer device 5. The second position P2 is a position where the substrate W is inspected by macro observation. The third position P3 is a position where the substrate W is delivered from/to the micro inspection unit 12. Sensors 25, 26, and 27 that detect the existence or the position of the substrate W at respective positions are provided at the first, second, and third positions P1, P2, and P3, respectively. For example, optically transmissive sensors or optically reflective sensors are used as the sensors 25 to 27. The two sensors 25 positioned at the first position P1 detect the amount of deviation from the substrate center, which is used as a reference, when the robotic transfer device 5 moves to a reference position above the arm portion 23 in placing the substrate W on the arm portion 23 in order to perform pre-alignment. That is, the amount of deviation from the substrate center used as a reference can be detected by using a table that stores output values of the amount of light of the two sensors 25 and coordinates of positional deviation of the substrate W which correspond to each other. The sensor 27 positioned at the third position P3 serves to perform precise alignment and is used to perform detection and alignment of a notch by rotation of a stage 72 to be described later.

Furthermore, a top surface inspection device 31, which controls the position of the substrate W by rocking and rotating the substrate W so that an inspector present at a front side can observe and inspect a top surface of the substrate W at various angles, and a bottom surface inspection device 32, which makes a position control so that a bottom surface of the substrate W faces the inspector, are provided at the second position P2.

Figure 2:
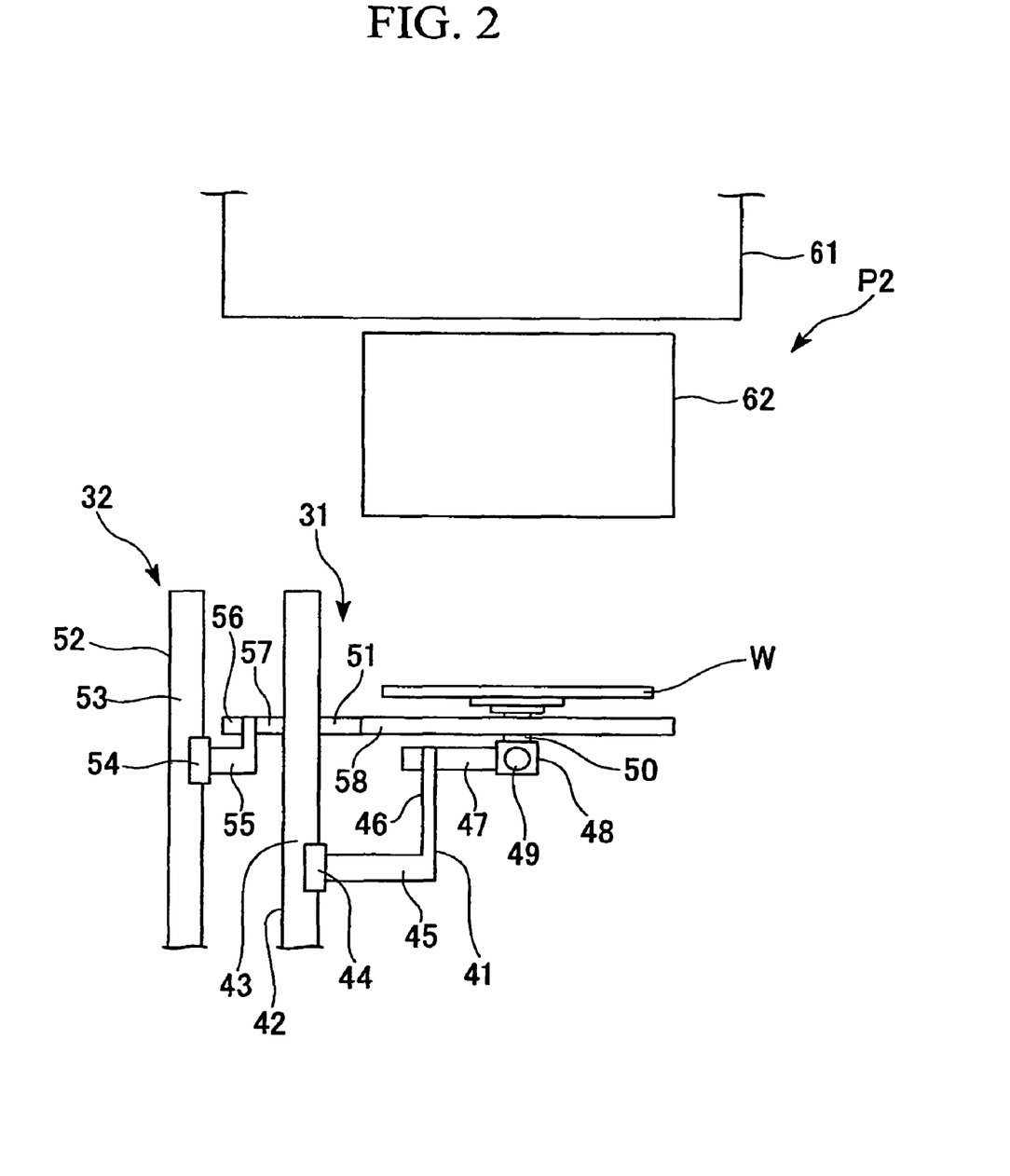
FIG. 2 is a view illustrating the arrangement of a top surface inspection device and a bottom surface inspection device as viewed from the arrow A in FIG. 1.

In addition, as shown in FIG. 2, an illuminating device 61 for macro observation serving to illuminate the substrate W is provided above the second position P2. FIG. 2 illustrates a view seen from an arrow A, which is viewed from an observer side.

As shown in FIGS. 1 and 2, the top surface inspection device 31 includes a first substrate holding portion 41 that holds the substrate W and a first substrate holding portion moving mechanism 42 that supports the first substrate holding portion 41 to freely move up and down. The first substrate holding portion moving mechanism 42 has a strut portion 43 extending in the vertically upward direction. A slider 44 is attached to the strut portion 43 such that the slider 44 is free to move up and down in the longitudinal direction of the strut portion 43. Although schematically shown in the drawing, a ball screw, a linear motor, and the like may be properly used as a mechanism for moving the slider 44 up and down. The first substrate holding portion 41 is attached to the slider 44. The first substrate holding portion 41 has an arm 45 extending from the slider 44. The arm 45 is bent approximately in an L shape in the vertically upward direction, and a rocking and rotation mechanism 46 is provided at the tip of the arm 45. The rocking and rotation mechanism 46 is configured to include a rotation bar 47, which is rotatably supported with respect to the arm 45, and a mechanism (not shown) that rotates the rotation bar 47. An axis line of the rotation bar 47 is disposed substantially horizontally and in a direction substantially perpendicular to a line L1 that connects an observer with the center of the substrate W. A rotation portion 48 is provided at the tip of the rotation bar 47. A rotary shaft 49 of the rotation portion 48 is disposed substantially horizontally and in a direction substantially perpendicular to the rotation bar 47 (parallel to the line L1 that connects an observer with the center of the substrate W in plan view). A support portion 50 that suctions and holds a substantially center of the bottom surface of the substrate W is attached on the rotation portion 48. The support portion 50 has an in-plane rotation mechanism for the substrate W around the center. Accordingly, the top surface inspection device 31 can make the substrate W inclined, rocked with two perpendicular axes as central axes, and rotating and moving up and down. In addition, the arm 45 has a shape so as not to interfere with the rotary transfer device 21 and the bottom surface inspection device 32 while the substrate W is being moved up and down.

The bottom surface inspection device 32 includes a second substrate holding portion 51 that holds the substrate W and a second substrate holding portion moving mechanism 52 that supports the second substrate holding portion 51 to freely move up and down. The second substrate holding portion moving mechanism 52 has a strut portion 53 extending in the vertically upward direction in the same manner as the first substrate holding portion moving mechanism 42, that is, extending in parallel to the substrate holding portion 41. A slider 54 is attached to the strut portion 53 such that the slider 54 is free to move up and down in the longitudinal direction of the strut portion 53. The second substrate holding portion 51 is attached to the slider 54. The second substrate holding portion 51 has an arm 55 extending from the slider 54.

A rotation mechanism 56 is attached to the arm 55. The rotation mechanism 56 is configured to include a rotation bar 57 and a mechanism, such as a stepping motor (not shown) for rotating the rotation bar 57.

A rotary axis of the rotation bar 57 is disposed substantially horizontally and in a direction substantially perpendicular to the line L1 that connects an observer with the center of the substrate W. A hand 58 is provided at the tip of the rotation bar 57 so that the outer edge of the bottom surface of the substrate W is suctioned and held. The hand 58 has an approximately arc shape in plan view. Three protruding portions 58A are provided at the arc such that three protruding portions 58A extend toward the center of the arc. A suction hole for suctioning the substrate W is formed on an upper surface of each of the protruding portions 58A. In such a bottom surface inspection device 32, it is possible to make the substrate W move up and down and inclined The origin position (initial position) of the hand 58 is substantially equal in height to the origin position of the support portion 24 and is lower than the origin position (initial position) of the support portion 50 of the top surface inspection device 31. The bottom surface inspection device 32 is configured not to interfere with the rotary transfer device 21 and the top surface inspection device 31. The top surface inspection device 31, the bottom surface inspection device 32, and the rotary transfer device 21 are all positioned at the initial positions except when they operate.

The illuminating device 61 for macro observation disposed above the top surface inspection device 31 and the bottom surface inspection device 32 includes a light source, a lamp (not shown) that causes light, which illuminates the substrate W from the above, to become diffused light or converging light, and an optical system having a Fresnel lens and a liquid crystal plate that switches a state of a diffusion plate between transmissive and transflective states by ON/OFF operation of a power source. In addition, a mirror 62 is disposed at a back side of the bottom surface inspection device 32 as viewed from an inspector. The mirror 62 is provided to be slightly inclined from the line L1 that connects the inspector with the substrate W in plan view. An imaging device 63 that is a macro capture apparatus is provided on the axis that passes through the center of the substrate W and is bent at the mirror 62. The mirror 62 and the imaging device 63 are positioned so as not to obstruct an operation of each device and visual observation.

The micro inspection unit 12 has a microscope 71 for performing an enlargement observation of a top surface of the substrate W and a stage 72 for holding the substrate W. The stage 72 is an XYθ stage and is configured to be able to convey the substrate W between a lower portion of an objective lens of the microscope 71 and the third position P3 and to rotate the substrate W. A plurality of objective lenses are attached to the microscope 71 such that the plurality of objective lenses can be switched, and the microscope 71 has a configuration in which an ocular 71A protrudes from a front surface of the main apparatus body 2. An enlarged image may be displayed on a display 73 or the like by providing an imaging device instead of the ocular 71A or together with the ocular 71A. In addition, a micro portion position sensor 75 for detecting the existence of the substrate W is provided in a region where the substrate W is disposed when making an observation with the microscope 71. For example, an optically transmissive sensor or an optically reflective sensor is used as the micro portion position sensor 75. An outer edge inspection device (not shown) that inspects the outer edge of the substrate W may be provided in the micro inspection unit 12.

The visual inspection apparatus 1 is controlled by a control unit 81. The control unit 81 is configured to include a CPU (central processing unit), a memory, and the like. The control unit 81 connects with an interface portion 82 that receives an inspector's operation, a control unit of the robotic transfer device 5, a control unit of the rotary transfer device 21, a control unit of the top surface inspection device 31, a control unit of the bottom surface inspection device 32, and a control unit of the micro inspection unit 12. In addition, various kinds of sensors 6, 25 to 27, and 75 are connected so that the position of the substrate W can be detected.

Next, an operation in the present embodiment will be described.

When inspecting the substrate W, the robotic transfer device 5 suctions, holds, and takes out the substrate W, which has not yet been inspected, from the wafer carrier 3 under the control of the control unit 81. After checking the existence of the substrate W by the wafer detecting sensor 6, pre-alignment is executed at the first position P1 that is a substrate delivery position by using the sensor 25. Then, the substrate W is delivered to the support portion 24 that is on standby. That is, a state of suction and holding performed by the robotic transfer device 5 is released and the substrate W is suctioned and held by the support portion 24, thereby returning the robotic transfer device 5 to an initial position. At this time, the position sensor 25 checks whether or not the substrate W is present on the support portion 24 that is positioned at the first position P1.

The control unit 81 drives the rotary transfer device 21 to move the substrate W, which is positioned at the first position P1, to the second position P2. The position sensor 26 is used to check whether or not the substrate W has arrived at the second position P2.

Figure 3:
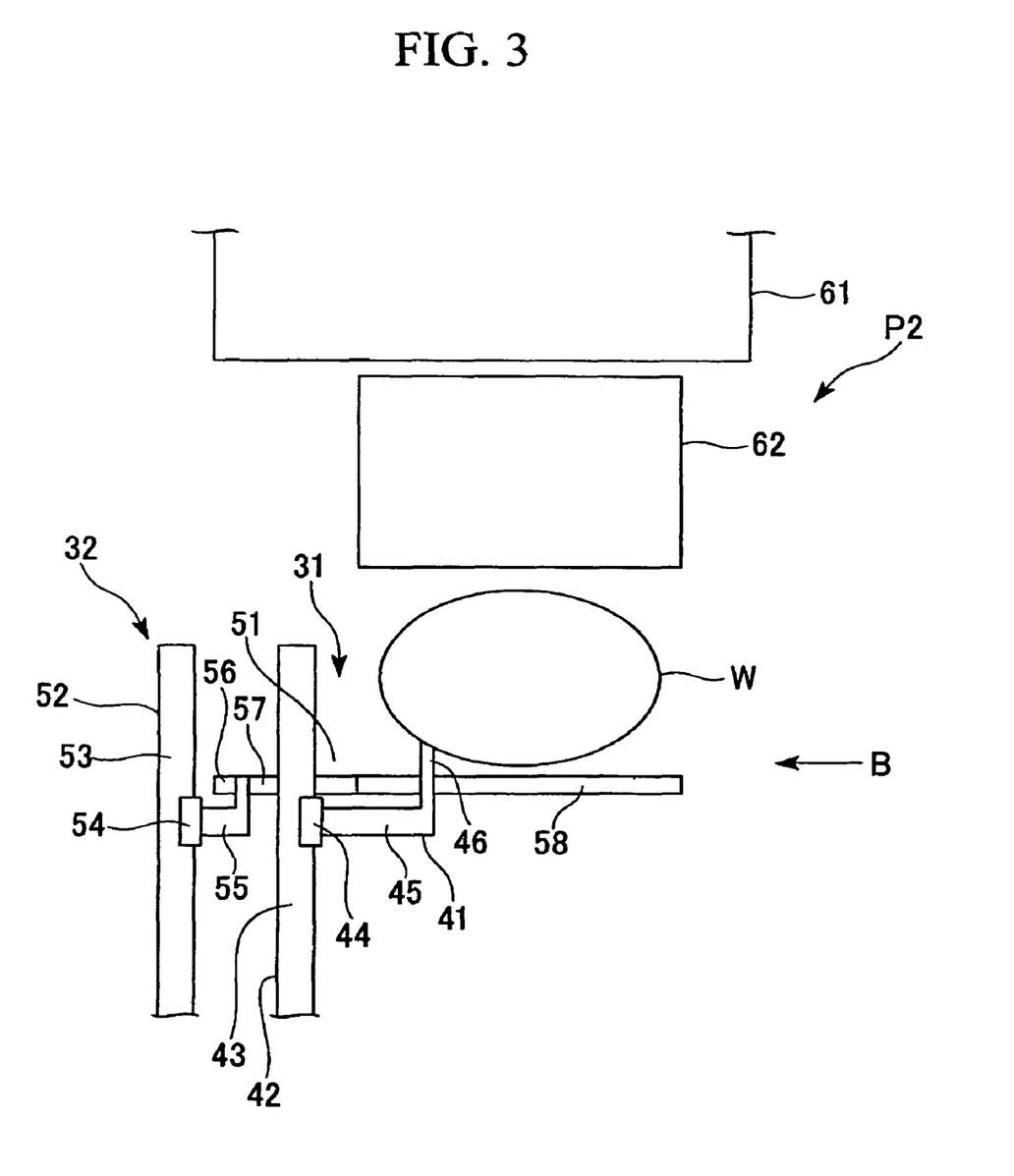
FIG. 3 illustrates a view in which a substrate is moved up to an inspection position with a top surface inspection device and is inclined toward an inspector.
Figure 4:
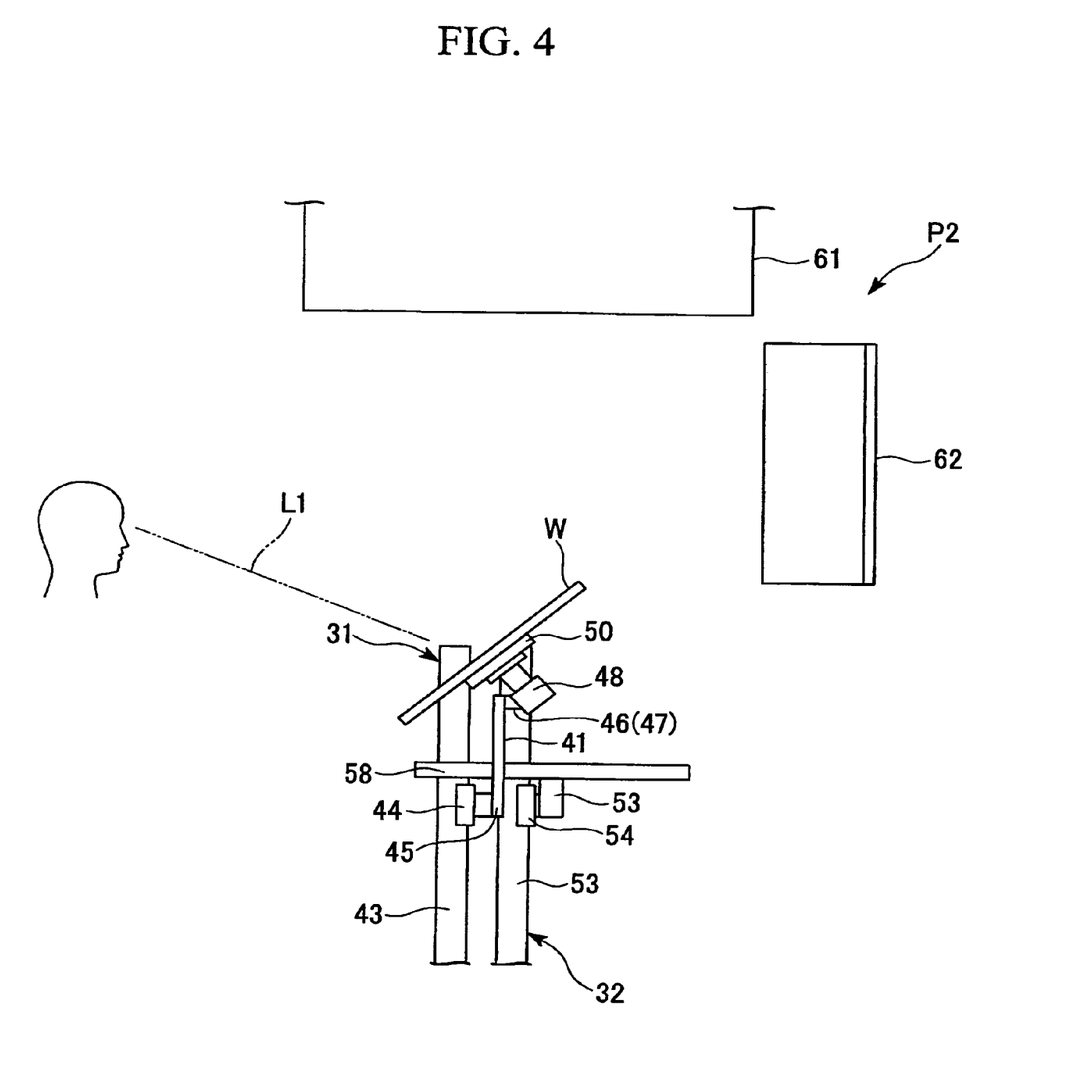
FIG. 4 illustrates a view seen from the arrow B in FIG. 3.

In the case of performing top surface inspection, suction and holding by the support portion 24 is released and then the support portion 24 is moved downward in order to move the substrate W to the support portion 50 of the top surface inspection device 31. After suctioning and holding the substrate W by the support portion 50 as shown in FIG. 2, the slider 44 is moved along the strut portion 43 in order to move the substrate W upward to the inspection position while maintaining a horizontal position. Then, as shown in FIGS. 3 and 4, the rotation bar 47 is rotated such that the substrate W is inclined by the algorithm or the like in which the inspection routine based on robot teaching is stored For example, a top surface of the substrate W at the inspection position is inclined toward the inspector. At this time, an inspector performs visual observation and inspection of a top surface of the substrate W in a state where the top surface of the substrate W is illuminated by the illuminating device 61 for macro observation. If necessary, the substrate W may be largely inclined in a state where the substrate W is held on the support portion 50 such that the bottom surface faces the observer and then the periphery of the bottom surface may be inspected. After the inspector's macro inspection using the top surface inspection device 31 is completed, the substrate W returns to the substantially horizontal position by a command of the control unit 81.

Subsequently, when executing bottom surface inspection, the bottom surface inspection device 32, that is on standby at the lower position, at which there is no interference, at the time of inspection with the top surface inspection device 31, is moved upward until the bottom surface inspection device 32 reaches up to substantially the same height as the top surface inspection device 31 by moving the slider 54 along the strut portion 53. Then, the top surface inspection device 31 delivers the substrate W to the arm 55 of the bottom surface inspection device 32 by releasing the suction by the support portion 50 and then moving the support portion 50 downward. The bottom surface inspection device 32 suctions and holds the outer edge of the substrate W on the arm 55.

The inspection position at this time is controlled by the control unit 81 such that the inspection position at this time is substantially equal to the inspection position in the top surface inspection device 31.

In addition, the positions of the support portion 50 and the rotation bar 47 deviate from each other in the top surface inspection device 31, while the axis line of the hand 58 and the axis line of the rotation bar 57 substantially match each other in the bottom surface inspection device 32. For this reason, the central, position when making the substrate W inclined in the bottom surface inspection device 32 is different from that in the top surface inspection device 31. However, difference therebetween is preferably as small as possible and the central positions are made to substantially match each other by the control of the control unit 81, for example, the substrate central position at the time of top surface inspection and the substrate central position at the time of bottom surface inspection match each other. In the related art, since a rotary axis is positioned outside the radius of a substrate, it was necessary to move the substrate upward by 90° so that an observer can see a bottom surface. Accordingly, the position of the substrate center deviated more than the radius of the substrate. In contrast, in the visual inspection apparatus 1, the positional deviation between the substrate center at the time of top surface inspection and the substrate center at the time of bottom surface inspection falls within the radius of the substrate W. Accordingly, since the amount of movement of observer's eyes is small, the observer's burden is reduced.

Figure 5:
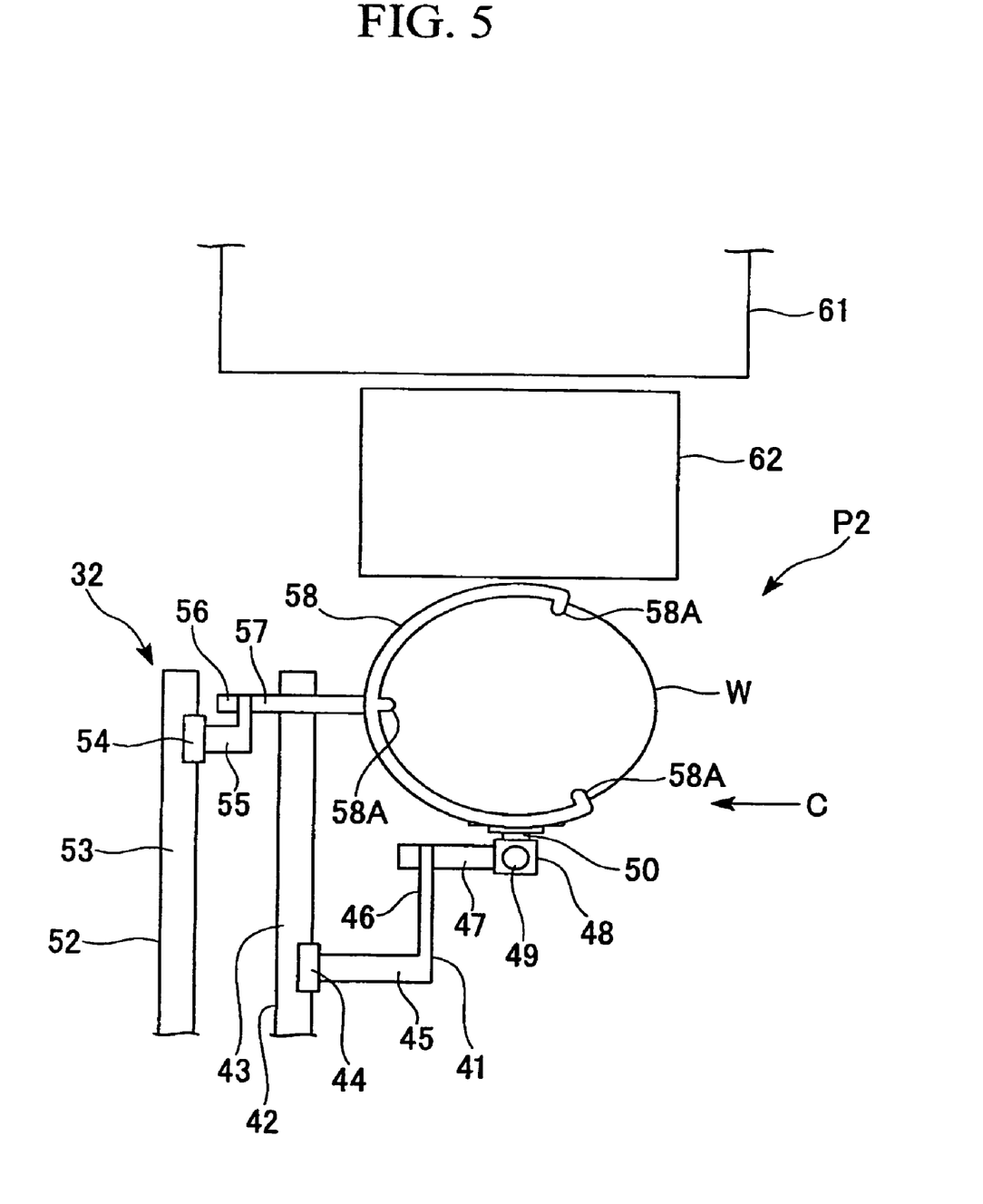
FIG. 5 illustrates a view in which a substrate is moved up to an inspection position with a bottom surface inspection device and is inclined toward an inspector.
Figure 6:
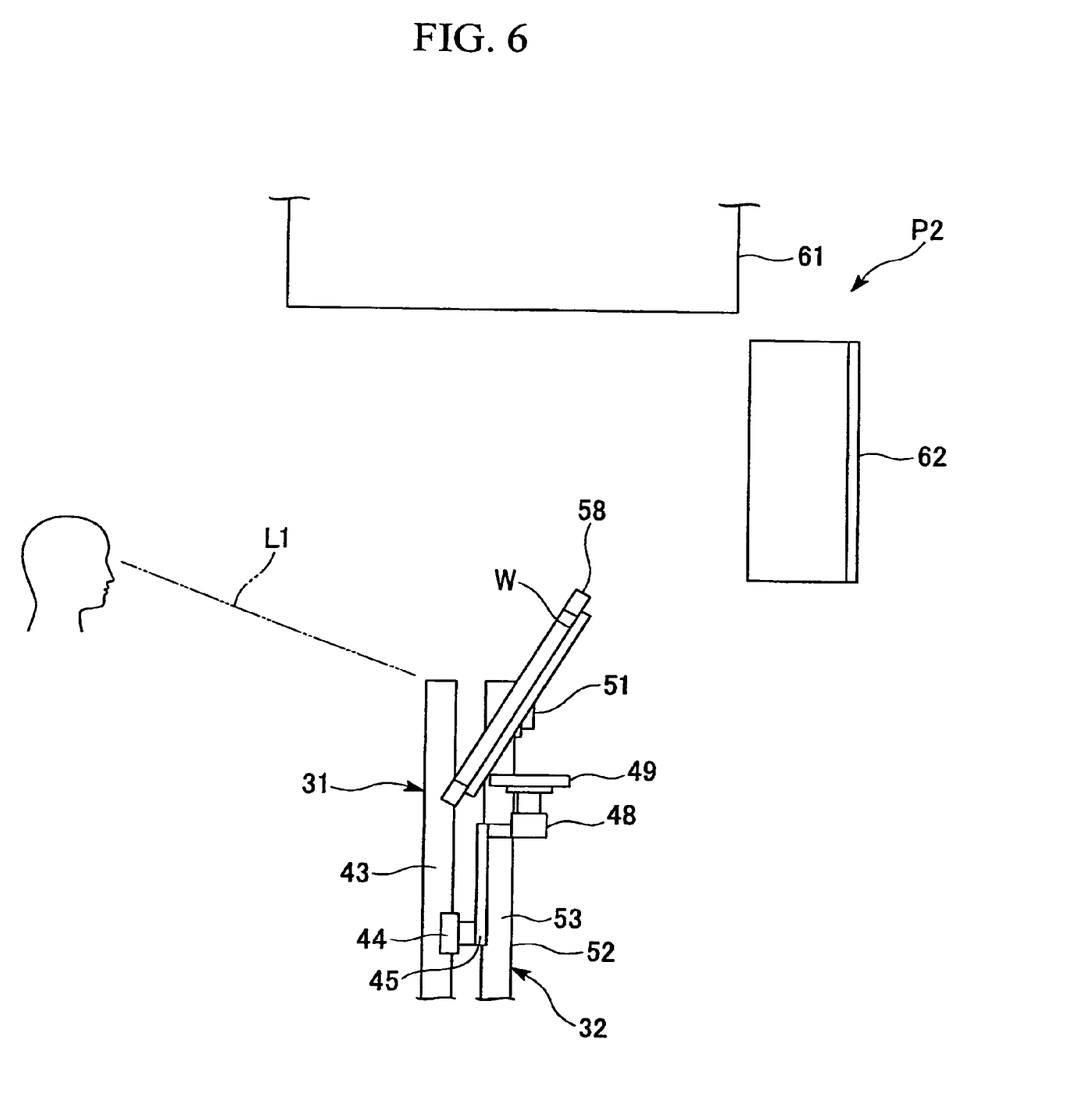
FIG. 6 is a view seen from the arrow C in FIG. 5.

As shown in FIGS. 5 and 6, the rotation bar 57 is rotated to make the bottom surface of the substrate W inclined toward the inspector while illuminating the bottom surface of the substrate W with the illuminating device 61 for macro observation. The inspector performs visual observation and inspection of the bottom surface of the substrate W. After the inspector's macro inspection using the bottom surface inspection device 32 is completed, the substrate W returns to the substantially horizontal position and then is moved downward by the command of the control unit 81.

After the macro inspection is completed, the arm 55 is moved downward and the support portion 24 is moved upward to move the substrate W to the support portion 24. When the substrate W is suctioned and held, the rotary transfer device 21 is driven to convey the substrate W to the position P3. It can be checked whether or not the substrate W has been conveyed to the third position P3 by using the position sensor 27. At the third position P3, the substrate W is delivered to the stage 72 of the micro inspection unit 12. When the delivery is performed, the stage 72 rotates the substrate W to detect the notch position and the amount of deviation of the central position of the substrate by the sensor 27. The stage 72 suctions and holds the substrate W thereon, aligns the notch position with a reference direction, and performs coordinate transformation of correction for eliminating the amount of deviation detected by the sensor 27, thereby moving the substrate W to an observation region of the microscope 71. After the micro portion position sensor 75 detects the existence of the substrate W, micro observation using the microscope 71 is performed. After the inspector completes the micro inspection, the stage 72 is moved to return the substrate W to the third position P3. At the third position P3, the substrate W is delivered from the stage 72 to the rotary transfer device 21. The delivery of the substrate W is checked by the position sensor 27. When the rotary transfer device 21 is driven, the substrate W is conveyed to the first position P1. Then, the robotic transfer device 5 takes out the substrate W from the first position P1 and the substrate W is received in the wafer carrier 3.

When one substrate W is conveyed from the first position P1 to the second position P2, the support portion 24 that has moved to the first position P1 is vacant. Accordingly, the next substrate W is conveyed to the support portion 24. Since there are three support portions 24 in the rotary transfer device 21, a maximum of three substrates W can be handled at the same time. Accordingly, the plurality of substrates W can be continuously inspected by sequentially supplying the plurality of substrates W. The sequence or combination in inspection using the macro inspection unit 11 or the micro inspection unit 12 can be arbitrarily changed.

Here, a case in which an imaging device is used in addition to the visual inspection or instead of the visual inspection will be described.

Figure 7:
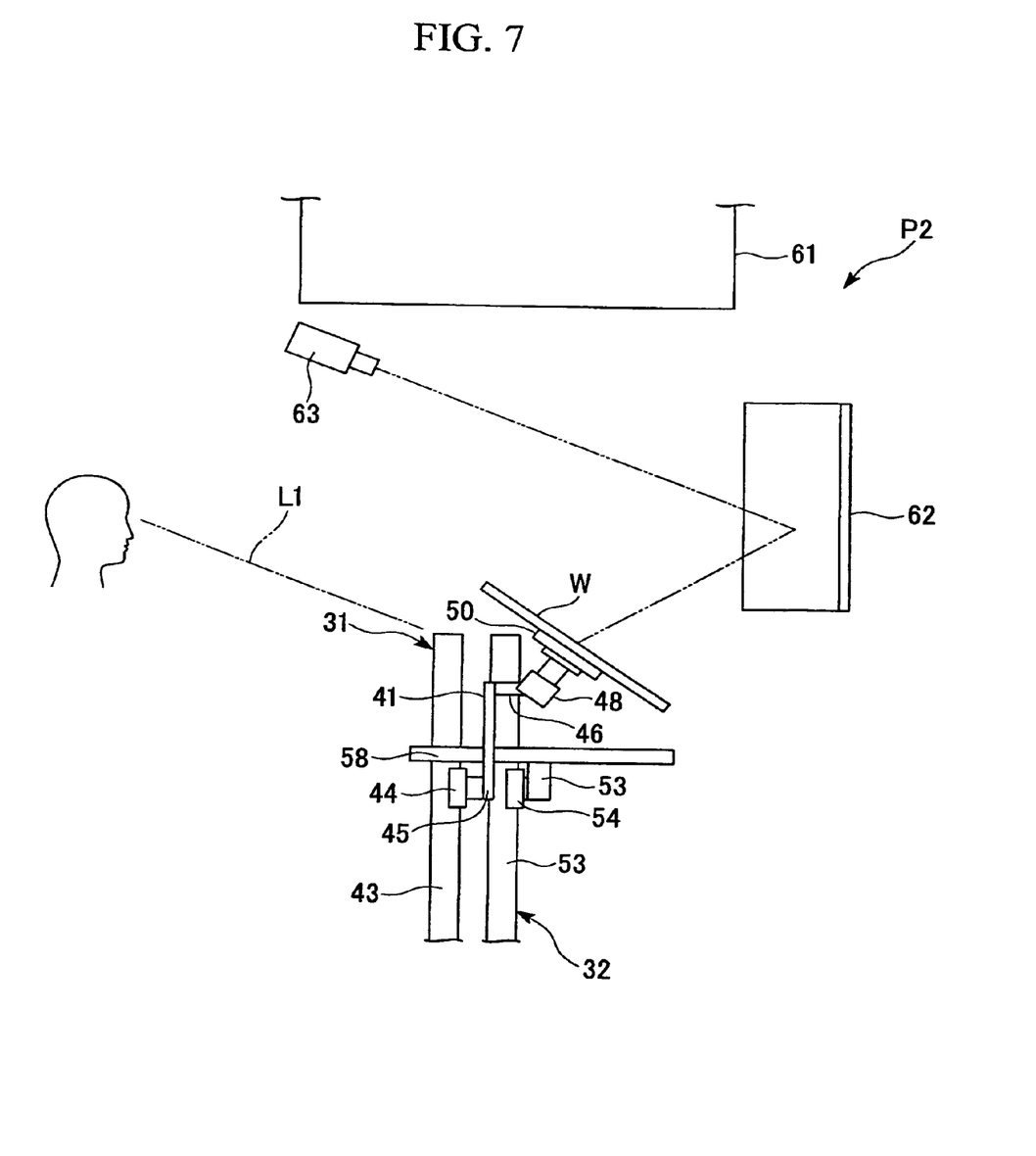
FIG. 7 illustrates a view in which a substrate is moved up to an inspection position with a top surface inspection device and is inclined toward a mirror.

The control unit 81 drives the rocking and rotation mechanism 46 of the top surface inspection device 31 to make the top surface of the substrate W at the inspection position face toward the mirror 62. As shown in FIG. 7, since the top surface of the substrate W is disposed on the optical axis of the imaging device 63 bent by the mirror 62, a surface image of the substrate W can be acquired in the imaging device 63. In particular, the two inspection devices 31 and 32 are controlled such that only the direction of a line of sight of an observer is changed to the direction of an optical axis of the imaging device 63 while maintaining the relationship among three angles of the direction of the line of sight of the observer, the normal line direction with respect to a main surface of the substrate W, and the direction of an optical axis of the illuminating device 61 for macro observation. Thus, the same image as when observation is performed can be acquired. In addition, it is preferable to dispose the imaging device 63 such that the optical path length between the observer and the substrate W and the optical path length from the imaging device 63 to the substrate W are equal to each other if possible. More preferably, the imaging device 63 is disposed at the position where the two optical path lengths are substantially equal to each other.

Figure 8:
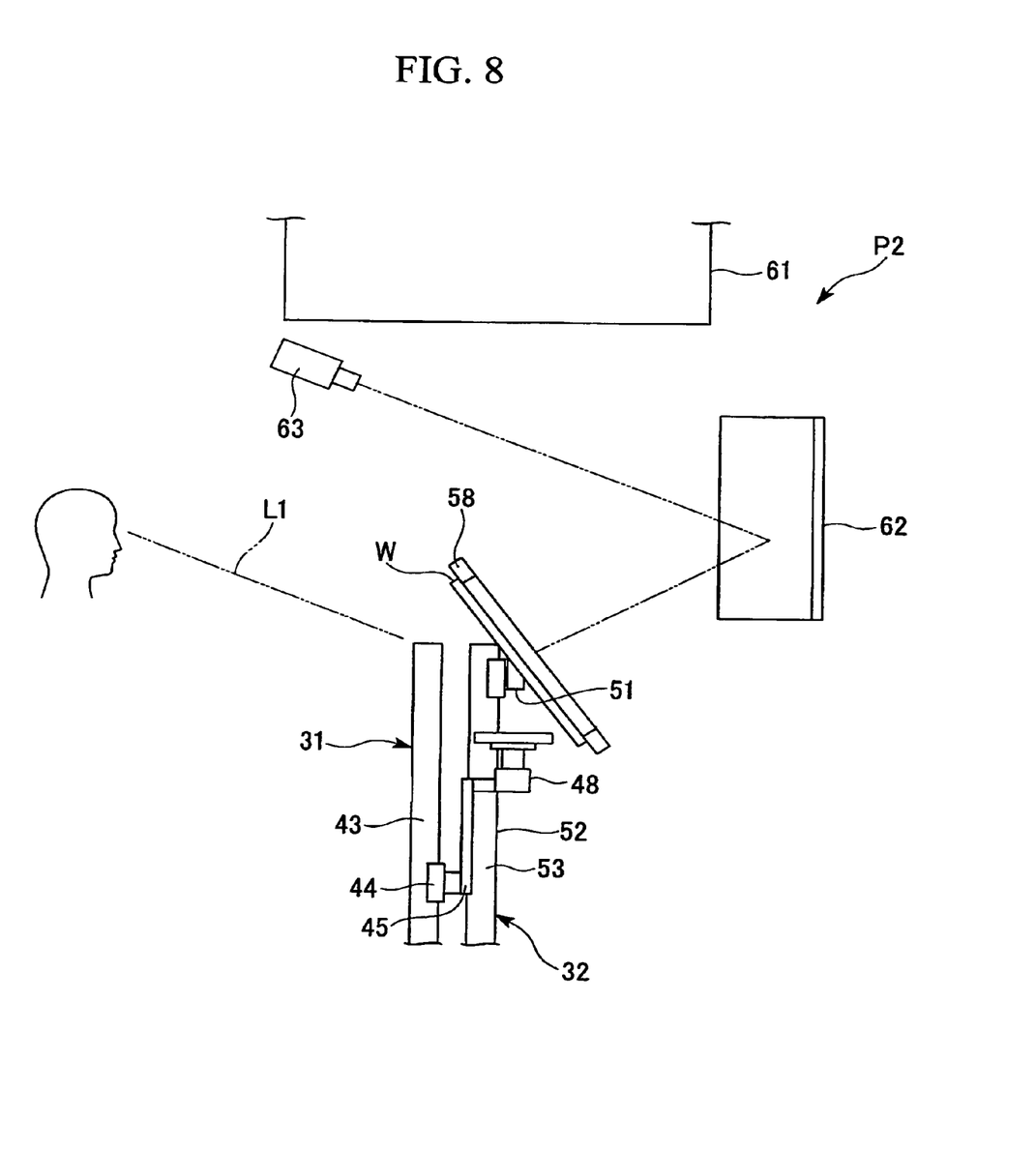
FIG. 8 illustrates a view in which a substrate is moved up to an inspection position with a bottom surface inspection device and is inclined toward a mirror.

When acquiring a bottom surface image of the substrate W, the substrate W is delivered to the bottom surface inspection device 32 and the rotation mechanism 56 at the substantially equal inspection position is driven to make the substrate W face toward the mirror 62. As shown in FIG. 8, since the bottom surface of the substrate W is disposed on the optical axis of the imaging device 63 bent by the mirror 62, a bottom surface image of the substrate W can be acquired in the imaging device 63.

A top surface image or a bottom surface image acquired in the imaging device 63 may be displayed on a monitor or recorded in a recording device (not shown). In each of the top surface inspection and the bottom surface inspection, an angle of inclination of the substrate W may be equal to each angle of inclination at the time of visual observation or may be changed to an angle of inclination such that a difference of arrangement between an inspector and the imaging device 63 is eliminated. The change in the angle of inclination is made by the control of the control unit 81. An image reflected by the mirror 62 is a reversal image of an actual object Accordingly, the control unit 81 reverses a captured image by image processing in order to display or record an image disposed correctly.

Since the bottom surface inspection device 32 is configured such that the peripheral edge of the substrate W is supported by the protruding portion 58A, the bottom surface inspection device 32 cannot photograph a bottom surface image of the substrate W at a portion matching the protruding portion 58A. Accordingly, the substrate W may be delivered to the top surface inspection device 31 after imaging a bottom surface image. Then, after rotating the substrate W by a predetermined angle, the substrate W may be held again in the bottom surface inspection device 32 to thereby perform imaging. The angle of rotation at this time is an angle that allows a portion hidden in the protruding portion 58A at the time of first imaging to be exposed and an already imaged portion to be suctioned and held on the protruding portion 58A. The control unit 81 stores the angle by which the substrate W is rotated, and mixes a first bottom surface image with a second bottom surface image by image processing to create a clear bottom surface image.

According to the present embodiment, the inspection positions in the top surface inspection device 31 and the bottom surface inspection device 32 are arranged to be substantially equal to each other by the control of the control unit 81. As a result, since an inspector can perform inspection without largely moving his or her eyes, the inspector's burden can be reduced. Although the position of the substrate W may slightly deviate due to a difference between apparatus configurations of the top surface inspection device 31 and the bottom surface inspection device 32, the inspector's burden is sufficiently reduced by setting the difference of inspection position to be equal to or smaller than the radius of the substrate W. Examples of a configuration in which the difference of inspection position is set to be equal to or smaller than the radius of the substrate W include a case where the center of the support portion 50 and the center of the hand 58 substantially match in the vertical direction and a case where rotary axes are set in parallel.

Since the direction of an optical axis of the imaging device 63 is bent by the mirror 62, an observation corresponding to observer's observation may be performed by using the imaging device 63 or may be recorded even if the imaging device 63 is disposed to be very close to the observation position of the observer. Since the degree of freedom of the layout of the imaging device 63 can be increased, the visual inspection apparatus 1 can be made small. In addition, compared with a case where a mechanism for changing the optical axis of an imaging device or a mechanism for adjustment of a focal point is provided or a plurality of cameras are mounted, apparatus cost can be reduced.

Moreover, in the case where there is no restriction in the layout of an apparatus, an imaging device positioned at an extending line of a line that connects an inspector with the center of a substrate in plan view may also be disposed at a rear side of the visual inspection apparatus 1. In this case, it becomes not necessary to provide the mirror 62.

Second Embodiment

Figure 9:
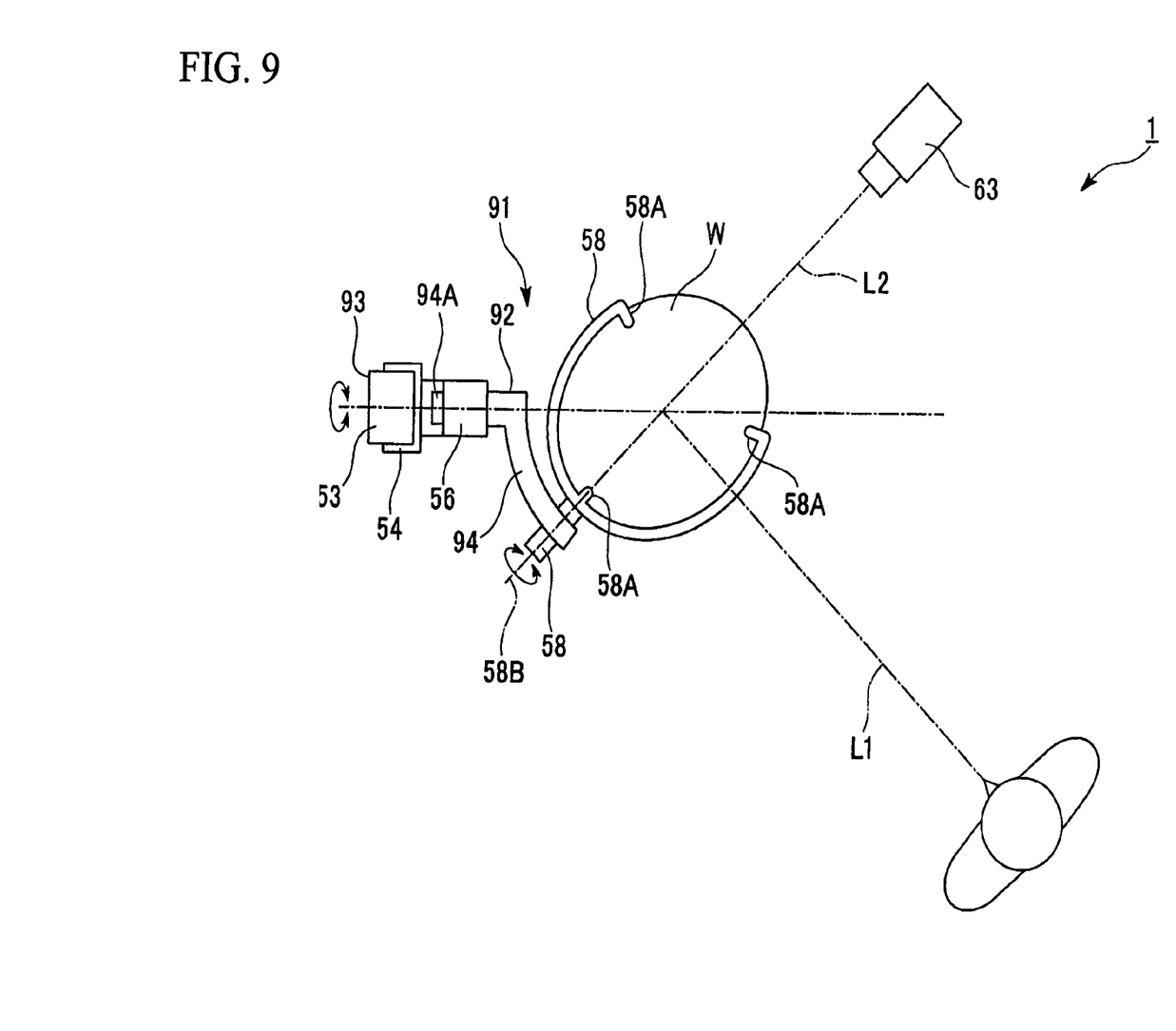
FIG. 9 is a plan view illustrating a bottom surface inspection device according to a second embodiment, which shows a view in which a substrate is inclined toward an inspector.

The configuration of a bottom surface inspection device is shown in FIG. 9. Other configurations are the same as those in the first embodiment.

A bottom surface inspection device 91 includes a second substrate holding portion 92 that holds a substrate W and a second substrate holding portion moving mechanism 93 that supports the second substrate holding portion 92 to freely move up and down.

The second substrate holding portion 92 has a hand 58 for holding the substrate W and an offset arm 94. The hand 58 is rotatably supported at an end of the offset arm 94 by a mechanism (not shown). In an initial state, a first rotary shaft 58B that rotates the hand 58 is disposed substantially horizontally and in a direction substantially perpendicular to a line L1 that connects the center of the substrate W with an observer who is present at a predetermined position in order to perform micro inspection at the time of micro inspection. The offset arm 94 extends in the shape of a circular arc substantially along the outer periphery of the substrate W and is rotatably supported by a rotation mechanism 56, such as a motor. A second rotary shaft 94A that rotates the offset arm 94 is set to be substantially horizontal and to pass through the approximate center of the substrate W on a plane that divides an angle, which is formed by the line L1 and a line L2 (optical axis direction of the imaging device 63 going toward the substrate center) in plan view, into two equal parts. In the present embodiment, the second rotary shaft 94A is inclined by 45° from the first rotary shaft 58B when the center of the substrate W is set as a reference. The rotation mechanism 56 is fixed to a slider 54 of the second substrate holding portion moving mechanism 93. Alternatively, the rotation mechanism 56 may be connected to the slider 54 of the second substrate holding portion moving mechanism 93 with another offset member provided therebetween in the case when an arrangement space of a strut portion 53 is restricted and the strut portion 53 cannot be disposed on the plane that divides an angle, which is formed by the optical axis direction of the imaging device 63 going toward the substrate center, and the line that connects the observer and the substrate center in the plan view, into two equal parts at the substrate center.

In the visual inspection apparatus 1, the imaging device 63 is disposed in the direction of the line L2 substantially perpendicular to the line L1. In the initial state, the direction of the line L2, which is also the optical axis direction of the imaging device 63, and the first rotary shaft 58B are disposed substantially on the same line in plan view.

Furthermore, also in the drawing seen from the side direction, the imaging device 63 is disposed such that an angle, at which the direction of a line of sight when an observer keeps his or her eyes toward the substrate center is inclined from the horizontal direction, and an angle, at which the optical axis direction of the imaging device 63 going toward the substrate center is inclined from the horizontal direction, are substantially equal to each other, in the same manner as in the first embodiment.

When performing the bottom surface inspection, the first rotary shaft 58B is disposed substantially horizontally and in a direction substantially perpendicular to the line L2 and the peripheral edge of the bottom surface of the substrate W is suctioned and held. The substrate W is moved upward to substantially the same inspection position as when the top surface inspection is performed and the hand 58 is rotated around the first rotary shaft 58B to make the bottom surface of the substrate W face the inspector.

Figure 10:
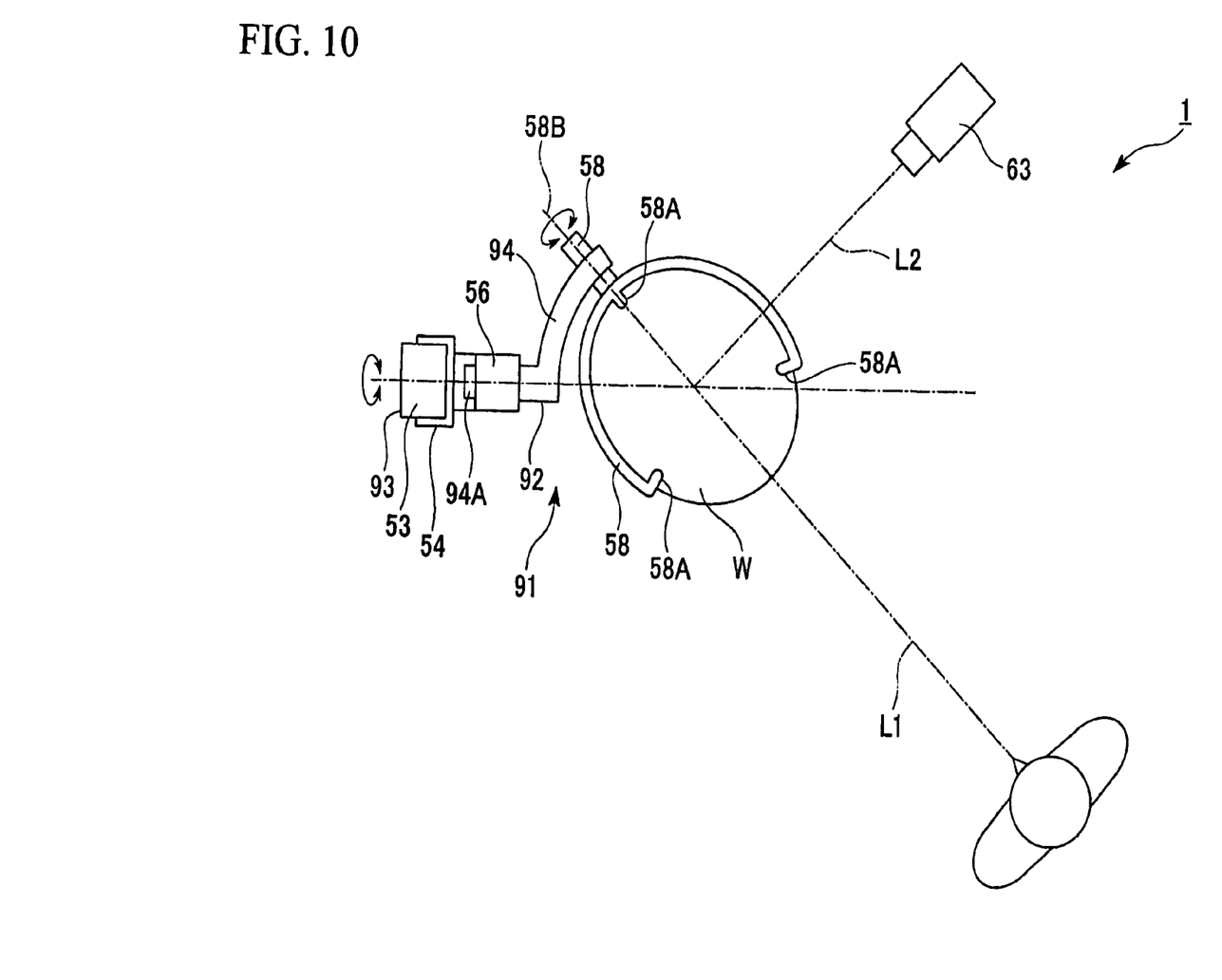
FIG. 10 is a plan view illustrating a bottom surface inspection device, which shows a view in which a substrate is inclined toward an imaging device.

After the visual inspection is completed, the control unit 81 fixes the first rotary shaft 58B and rotates the second rotary shaft 94A by 180° to rotate the second substrate holding portion 92. As shown in FIG. 10, in the present embodiment, the first rotary shaft 58B is disposed on an extending line of the line L1 in plan view. In addition, the first rotary shaft 58B is rotated to make the bottom surface of the substrate W inclined toward the imaging device 63. The first rotary shaft 58B is rotated such that the observation direction at the time of visual inspection and the optical axis direction of the imaging device 63 are substantially equal to each other. The imaging device 63 acquires a bottom surface image and displays the bottom surface image on a monitor or records the bottom surface image. The first rotary shaft 58B may be first rotated to make the substrate W positioned horizontally or at other angles and then the second rotary shaft 94A may be rotated by 180°. Alternatively, the second rotary shaft 94A and the first rotary shaft 58B may also be rotated at the same time.

Thus, the relationship among three angles of the optical axis direction of the illuminating device 61 for macro observation at the time of visual observation, the normal line direction with respect to a main surface of the substrate W, and the direction of a line of sight of the observer can be made equal to the relationship among three angles of the optical axis direction of the illuminating device 61 for macro observation at the time of imaging using the imaging device 63, the normal line direction with respect to the main surface of the substrate W, and the optical axis direction of the imaging device 63. Accordingly, substantially the same inspection image as when visual observation is performed can be obtained.

In the present embodiment, since the bottom surface inspection device 91 has the two rotary shafts 58B and 94A, the bottom surface of the substrate W can be changed by 90° about vertical axis. Accordingly, by disposing the imaging device 63 at the position deviating by 90° from the inspector, substantially the same image as when visual observation is performed can be easily obtained as a bottom surface image. In addition, since it becomes easy to dispose the imaging device 63 in a space that is vacant within the visual inspection apparatus 1, the apparatus can be easily made small. In addition, since a mechanism for inclination to two axes is provided in the top surface inspection device 31, the surface of the substrate W can be made to face toward the imaging device 63. Accordingly, by making a control such that the inspection positions are substantially equal, a top surface image and a bottom surface image can be acquired by one imaging device 63.

The invention may be widely applied without being limited to the above embodiments.

For example, the visual inspection apparatus 1 may be configured not to include the micro inspection unit 12.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

According to the aspect of the present invention, the substrate position at the time of top surface inspection and the substrate position at the time of a bottom surface inspection are controlled to be substantially equal to each other. As a result, since the amount of movement of observer's eyes can be reduced when visually inspecting the top and bottom surfaces of the substrate, an inspector's burden is reduced. In addition, since a substrate inspection result can be recorded by one imaging device, the configuration of the apparatus can be simplified. As a result, the apparatus can be manufactured at a low cost.

What is claimed is:

1. A visual inspection apparatus comprising:
    a first substrate holding portion that is adapted to apply suction and hold substantially a center of a bottom surface of a substrate so that a top surface of the substrate is observable;
    a second substrate holding portion that is different from the first substrate holding portion and that is adapted to apply suction and hold an outer edge of the substrate so that the bottom surface of the substrate is observable;
    a first substrate holding portion moving mechanism that moves the first substrate holding portion;
    a second substrate holding portion moving mechanism that moves the second substrate holding portion; and
    a control device that controls the first substrate holding portion moving mechanism and the second substrate holding portion moving mechanism so that a position of the substrate when observing the top surface of the substrate in the first substrate holding portion substantially matches a position of the substrate when observing the bottom surface of the substrate in the second substrate holding portion.

2. The visual inspection apparatus according to claim 1, wherein the first substrate holding portion includes a rocking and rotation mechanism capable of rotating and rocking the substrate.

3. The visual inspection apparatus according to claim 1, wherein the second substrate holding portion comprises:
    a hand for holding a peripheral edge of the substrate, and
    a rotation mechanism for rotating the substrate and the hand together.

4. The visual inspection apparatus according to claim 3, wherein a rotary axis of the hand is provided on a line passing through a approximate center of the substrate.

5. The visual inspection apparatus according to claim 4, wherein the rotary axis of the hand is provided in a direction substantially perpendicular to a line that connects the substrate with an inspector.

6. The visual inspection apparatus according to claim 5, wherein a second rotary axis that rotates the second substrate holding portion is provided on a plane that divides an angle into two equal parts at a substrate central position, wherein the angle is formed by: (i) an optical axis direction of an imaging device capable of imaging the top and bottom surfaces of the substrate, and (ii) a line that connects a substrate center and an observer.

7. The visual inspection apparatus according to claim 1, wherein the first substrate holding portion moving mechanism and the second substrate holding portion moving mechanism are configured independently.

8. The visual inspection apparatus according to claim 7, wherein the first substrate holding portion moving mechanism and the second substrate holding portion moving mechanism include strut portions extending in parallel in a movement direction of the first substrate holding portion and the second substrate holding portion.

9. The visual inspection apparatus according to claim 1, wherein a central position of the substrate when observing the top surface of the substrate in the first substrate holding portion and a central position of the substrate when observing the bottom surface of the substrate in the second substrate holding portion fall within a radius of the substrate.

10. The visual inspection apparatus according to claim 1, further comprising an imaging device capable of imaging the top and bottom surfaces of the substrate.

* * * * *